United States Patent [19]

Briggs

[11] Patent Number: 4,853,356

[45] Date of Patent: Aug. 1, 1989

[54] PROCESS FOR TRIMERIZATION

[75] Inventor: John R. Briggs, South Charleston, W. Va.

[73] Assignee: Union Carbide Corporation, Danbury, Conn.

[21] Appl. No.: 234,610

[22] Filed: Aug. 22, 1988

Related U.S. Application Data

[60] Continuation of Ser. No. 873,708, Jun. 12, 1986, abandoned, which is a division of Ser. No. 839,638, Mar. 14, 1986, Pat. No. 4,668,838.

[51] Int. Cl.$^4$ .......................... B01J 31/14; C08F 4/62
[52] U.S. Cl. .................................... 502/117; 585/513; 585/512
[58] Field of Search .......................... 502/117

[56] References Cited

U.S. PATENT DOCUMENTS

| | | | |
|---|---|---|---|
| 3,008,985 | 5/1963 | Wilke | 585/512 |
| 3,242,099 | 3/1966 | Manyik et al. | 502/117 |
| 3,347,840 | 10/1967 | Manyik et al. | 585/512 |
| 3,627,700 | 12/1971 | Zuech | 502/117 |
| 3,756,977 | 9/1973 | Yoshimoto et al. | 502/117 X |
| 4,564,660 | 1/1986 | Williams et al. | 526/106 |

FOREIGN PATENT DOCUMENTS

| | | | |
|---|---|---|---|
| 1078108 | 9/1957 | Fed. Rep. of Germany | 585/512 |
| 7127525 | 11/1967 | Japan | 526/141 |
| 1084886 | 1/1975 | Japan | 526/100 |

OTHER PUBLICATIONS

Manyik et al., J. Catalysis, 47, (1977), pp. 197–209.

*Primary Examiner*—Patrick P. Garvin
*Attorney, Agent, or Firm*—Saul R. Bresch

[57] ABSTRACT

A process for the trimerization of an olefin selected from the group consisting of ethylene, propylene, 1-butene, and mixtures thereof comprising passing the olefin in contact with a catalyst comprising the reaction product of (i) a chromium compound, which will provide active catalytic species under trimerization conditions; (ii) a hydrocarbyl aluminum hydrolyzed with about 0.8 to about 1.1 moles of water per mole of aluminum compound; and (iii) a donor liquid selected from the group consisting of hydrocarbyl isonitriles, amines, and ethers wherein the aluminum to chromium mole ratio is in the range of up to about 200 to one and the ligand to chromium mole ratio is in the range of up to about 100 to one.

11 Claims, No Drawings

PROCESS FOR TRIMERIZATION

This application is a continuation of prior U.S. application: Ser. No. 873,708, filing date June 12, 1986 and now abandoned and/which is a division of application Ser. No. 839,638, filing date Mar. 14, 1986 and now U.S. Pat. No. 4,668,838.

TECHNICAL FIELD

This invention relates to a process for the trimerization or cotrimerization of ethylene, propylene, and 1-butene, a catalyst therefore, and a process for preparing the catalyst.

BACKGROUND ART

Processes for the catalytic polymerization of the above-mentioned olefins are well known. One process of particular interest here is that described in U.S. Pat. No. 3,347,840, incorporated by reference herein. This patent raises the problem of the disadvantageous production of appreciable amounts of 1-hexene in the polymerization of ethylene, and suggests various compounds to counter or inhibit this unwanted trimerization, which detracts from the efficiency of the conversion to polyethylene.

It was apparent, however, that the catalyst utilized in the process,e.g., a chromium (III) salt, usually an alkanoate, in combination with a partially hydrolyzed aluminum alkyl, such as triisobutyl aluminum, was capable of producing 1-hexene, albeit in minor amounts, for example, ten to 20 percent by weight of the ethylene consumed, and much of the 1-hexene was incorporated into the polymer. This observation suggested that the ethylene polymerization catalyst could be used to trimerize ethylene in greater than the minor amounts mentioned provided that, instead of 1-hexene inhibitors, 1-hexene promoters could be found. In this vein, the above patent alludes to components, such as deimthoxyethane, which tend to increase the amount of ethylene converted to 1-hexene. There is no indication that the conversion would be at all efficient, however, and, in fact, following the teachings of the patent, it is not.

DISCLOSURE OF INVENTION

An object of this invention, therefore, is to provide a process for the trimerization or cotrimerization of ethylene, propylene, and 1-butene wherein a high conversion of olefin to trimer is achieved.

Other objects and advantages will become apparent hereinafter.

According to the present invention, a process for the trimerization of an olefin selected from the group consisting of ethylene, propylene, 1-butene, and mixtures thereof has been discovered comprising passing the olefin in contact with a catalyst comprising the reaction product of (i) a chromium compound, which will provide active catalytic species under trimerization conditions, (ii) a hydrocarbyl aluminum hydrolyzed with about 0.8 to about 1.1 moles of water per mole of aluminum compound; and (iii) a donor ligand selected from the group consisting of hydrocarbyl isonitriles, amines, and ethers wherein the aluminum to chromium mole ratio is in the range of up to about 200 to one and the ligand to chromium mole ratio is in the range of up to about 100 to one.

DETAILED DESCRIPTION

Selectivity to trimer, in subject process when applied to the trimerization of ethylene, can be as high as eighty-five percent by weight or even higher based on the weight of ethylene reacted. With regard to ethylene, there is no significant production of branched trimer and almost all of the trimer is linear and terminal. Insofar as trimers and cotrimers of ethylene, propylene, and butene-1 are concerned, virtually little or no incorporation of trimer into the polyolefin by-product occurs. This can be verified by carbon-13 nuclear magnetic resonance spectroscopy and resin density measurements. Thus, there is produced what may be referred to as "free" trimer. Consequently, little or no separation of the desired product from other contaminating olefins is necessary. Essentially all of the trimer produced is recovered and it is of high quality with very little isomerization to the less desirable internal olefins. The major inefficiency is the formation of polyolefin homopolymer. Other low molecular weight oligomers are produced, e.g., in the production of 1-hexene, 1-butene and undefined octenes are produced, but these amount to less than about five percent by weight of the ethylene consumed.

The trimers produced by subject process are 1-hexene; nonenes; and dodecenes. Terminal 1-hexene is a desirable product for a number of applications, including copolymerization with ethylene and hydroformylation. It is advantageously used as a comonomer with ethylene since it imparts good tear strength to low density resins and has the required volatility and polymer incorporation properties. Terminal nonenes and dodecenes find a variety of applications similar to those of other long chain alpha-olefins such as in surfactants and lubricants.

The catalyst utilized in subject process is comprised of three components:

1. The first component is a chromium compound, which will provide active catalytic species under trimerization conditions. It is understood that the chromium compound can be a mixture of chromium compounds. The chromium can be in the oxidation states of 0 to 6 with the oxidation states (II), (III), and (IV) being preferred. The non-metallic portion of the compound can be inorganic or organic. A typical formula for the chromium compound is $CrX_n$ wherein X is an inorganic or organic radical and n is an integer from 1 to 6. The inorganic radical can be, for example, a halide, a sulfate, or an oxide. Halides are not preferred, however. The organic radical can have 1 to 20 carbon atoms, preferbly 1 to 10 carbon atoms, and can be selected from the group consisting of alkoxy, ester, or ketone radicals. The organic radicals can be straight chained or branched, cyclic or acyclic, aromatic or aliphatic, or can be made up of mixed aliphatic, aromatic, and/or cycloaliphatic groups. Preferred chromium compounds are as follows: chromium (III) tris(2-ethylhexanoate); chromium (II) bis(2-ethylhexanoate); and chromium (IV) tetra-tertiary-butoxide. Other suitable chromium compounds are chromous bromide; chromic bromide; chromous chloride, chromic chloride; chromous fluoride; chromic fluoride; chromium (II) acetate; chromium (III) oxy-2-ethylhexanoate; chromium (III) dichloroethylhexanoate; chromium (III) acetylacetonate; chromium (III) acetate; chromium (II) butyrate; chromium (III) butyrate; chromium (II) neopentanoate; chromium (III) neopentanoate; chromium (II) laurate;

chromium (III) laurate; chromium (II) stearate; chromium (III) stearate; chromium (II) oxalate; and chromium (III) oxalate. In a homogeneous process, the chromium compound must be soluble in the trimerization medium under trimerization conditions.

2. The second component is a hydrocarbyl aluminum hydrolyzed with about 0.8 to about 1.1 moles of water per mole of aluminum compound. The hydrocarbyl aluminum can be represented by the formula $R_3Al$ wherein each R is an alkyl, cycloalkyl, aryl, or hydride radical; at least one R is a hydrocarbyl radical; two or three R radicals can be joined in a cyclic radical forming a heterocyclic structure; each R can be alike or different; and each R, which is a hydrocarbyl radical, has 1 to 20 carbon atoms, and preferably 1 to 10 carbon atoms. Further, each alkyl radical can be straight or branched chain and such hydrocarbyl radical can be a mixed radical, i.e., the radical can contain alkyl, aryl, and/or cycloalkyl groups. Examples of suitable radicals are: methyl, ethyl, propyl, isopropyl, butyl, isobutyl, tert-butyl, pentyl, neopentyl, hexyl, 2-methylpentyl, heptyl, octyl, isooctyl, 2-ethylhexyl, 5,5-dimethylhexyl, nonyl, decyl, isodecyl, undecyl, dodecyl, phenyl, phenethyl, methoxyphenyl, benzyl, tolyl, xylyl, naphthyl, methylnaphthyl, cycohexyl, cycloheptyl, and cyclooctyl. It is understood that the donor ligand described below can be incorporated into the hydrocarbyl aluminum structure such that the hydrocarbyl radical includes isonitriles, amines, and ethers.

The hydrolyzed hydrocarbyl aluminum is also known as an aluminoxane, which is thought to be a complex mixture of unknown stoichiometry.

The synthesis can be described by the following equation:

$$nR_3Al + nH_2O \rightarrow (RAlO)_n + 2nRH.$$

A typical hydrolysis can be carried out at atmospheric pressure at a temperature in the range of about 0° C. to about 100° C., and preferably at a temperature in the range of about 10° C. to about 65° C. Water is added to a solution of, for example, trialkyl aluminum in an anhydrous, inert, organic solvent. The concentration varies from about 5 percent by weight aluminum compound to about 75 percent by weight based on the total weight of the solution. The water is preferably added slowly, but in a single batch, with vigorous stirring and cooling. The reaction is considered complete when effervescence ceases.

Another method for preparation of the aluminoxane is accomplished by using the waters of hydration of metal salts, e.g., by adding about 0.1 to about 0.16 mole of solid magnesium sulfate heptahydrate to a ten percent solution of triisobutyl aluminum in heptane. The mixture is stirred vigorously until effervescence ceases, usually overnight.

The solutions are stored under an inert gas such as argon.

Examples of suitable solvents are heptane, 1-hexene, hexane, pentane, isooctane, purified kerosene, cyclopentane, cyclohexane, methylcyclopentane, and dimethylcyclopentane. The use of 1-hexene is found to be advantageous in some cases. Benzene, toluene, and xylene can be used, but are not preferred. It will be understood that these solvents can be used both in the preparation of the chromium salt and the aluminoxane, and in the trimerization process itself, and that minor products of trimerization such as octenes will become part of the solvent on recycling.

Examples of hydrocarbyl aluminum compounds are as follows: triisobutylaluminum, trihexyl aluminum, di-isobutyl aluminum hydride, dihexyl aluminum hydride, isobutyl aluminum dihydride, hexyl aluminum dihydride, di-idobutylhexyl aluminum, isobutyl dihexylaluminum, trimethylaluminum, triethylaluminum, tripropylaluminum, triisopropylaluminum, tri-n-butylaluminum, trioctylaluminum, tridecylaluminum, tridodecylaluminum, tribenzylaluminum, triphenylaluminum, trinaphthylaluminum, and tritolylaluminum. The preferred hydrocarbyl aluminums are triisobutylaluminum, trihexyl aluminum, di-isobutyl aluminum hydride, and dihexyl aluminum hydride.

3. The third component belongs to a group of ligands, which can be characterized as electron donors. The ligands are compounds selected from the group consisting of hydrocarbyl isonitriles, amines, and ethers. Since a ligand can be a polymer, theoretically the number of carbons contained in its structure can be considered to be essentially unlimited. It is preferred, however, that each ligand have 1 to 20 carbon atoms. The hydrocarbyl portion of the ligand can be straight or branched chain alkyl, cycloalkyl, or aromatic, or a mixture of the foregoing. The ligands can be represented by a formula containing central donor atoms or groups, which are limited to the elements carbon, oxygen, and nitrogen. The formula follows:

$$(R)_mE[(R')_nE'(R)_{m'}]_a[(R')_{n'}E''(R)_{m''}]_b$$

wherein each R and R' is a straight or branched chain alkyl, cycloalkyl, or aromatic radical, or a mixture of the components which make up the foregoing radicals;

R and R' can be alike or different;

each E, E', and E" is a donor atom selected from the group consisting of oxygen, nitrogen, and an isonitrile carbon;

E, E', and E" can be alike or different;

m, m', m", n, and n' are integers from 0 to 3 selected to satisfy the valence requirements to the donor atoms;

any two R and/or R' radicals can be joined to form a single cyclic radical

R is bonded to one of E, E', or E";

R' is bonded to two of E, E', or E"; and a and b are any integers.

Examples of the application of the formula follows:

(i) for the monodentate ligand, diethyl ether:
R=ethyl, E=oxygen, m=2, a=0, and b=0; and (ii) for $CH_3O(CH_2CH_2O)_3CH_3$:
R=$CH_3$; R'=$CH_2CH_2$; each E, E', and E" is an oxygen atom; m=1; m'=0; m"=1; n=1; n'=1; a=2; b=1.

Ligands, which exhibit a high selectivity for free 1-hexene are as follows:

$CH_3O(CH_2CH_2O)CH_3$, also known as monoglyme
$CH_3O(CH_2CH_2O)_2CH_3$, also known as diglyme
$CH_3O(CH_2CH_2O)_3CH_3$, also known as triglyme
tert-butyl isonitrile
tetrahydrofuran
$C_6H_4(OCH_3)_2$, also known as veratrole.

Other useful ligands are tetramethylethylenediamine, 1,2-diethoxyethane, $CH_3O(CH_2CH_2O)_4CH_3$ also known as tetraglyme, 1,2 dimethoxypropane, 2,3 dimethoxybutane, o-diethoxybenzene, methylisonitrile, ethylisonitrile, phenylisonitrile, para-tolylisonitrile and tetraethylethylenediamine.

As noted, the aluminum to chromium mole ratio is in the range of up to about 200 to one. The preferred aluminum to chromium mole ratio is in the range of about one mole of aluminum to one mole of chromium to about 100 moles of aluminum to one mole of chromium with the lower ratios being preferred. Thus, the most preferred aluminum to chromium mole ratio is in the range of about one to one to about 50 to one. The ligand to chromium mole ratio is in the range of up to about 100 to one, and is preferably in the range of about one to one to about 100 to one. Within these ranges for the ligand to chromium mole ratio, each ligand has its own preferred range, which is determined experimentally. The optimum range for most ligands falls within the one to one to 40 to one range. Insofar as selectivity to free trimer is concerned, preferred ligands are selective in the range of 40 percent to 85 percent by weight or above based on the weight of olefin reacted. There is no preferred order for mixing the three components.

The three-component catalyst is effective in the trimerization process at temperatures in the range of 20° C. to about 200° C. Preferable temperatures are in the range of about 70° C. to about 140° C. Effective pressures are in the range of atmospheric to about 1500 psig or higher. Typical concentrations of chromium are in the range of about $10^{-3}$ millimoles per liter to about 10 millimoles per liter with other catalyst components scaled accordingly. The volume (measured in liters) referred to here includes the catalyst materials together with solvent, which will be utilized in the trimerization process.

The catalyst described in this specification is most easily employed in a homogeneous process such as that set out in the examples, but can be modified to operate as, for example, a heterogeneous silica-supported catalyst. Techniques such as those described in "Studies in Surface Science and Catalysis, Volume 8, Catalysis by Supported Complexes", edited by Yermakov, Elsevier Publishing Company, 1981, could be employed to achieve this objective.

The invention is illustrated by the following examples.

EXAMPLE I

All operations involving the use of catalyst components are conducted under an inert argon atmosphere. Heptane solvent is first stirred over concentrated sulfuric acid for 2 days to remove water, aromatics, and other unsaturates, then stored over and distilled under argon from calcium hydride or a sodium/potassium alloy before use. Other additives are purified in a conventional manner, e.g., monoglyme is distilled under argon from sodium metal and stored over molecular sieves in the dark. Ethylene is polymer grade. It is purified to polymerization process specifications and further dried by passage through molecular sieves.

Chromium (III) tris(2-ethylhexanoate) is typically prepared from anhydrous chromium (III) chloride and 2-ethylhexanoic acid as follows: About 110 cubic centimeters (cc.) of 2-ethylhexanoic acid is heated to 130° C. and sparged with argon for about 2 hours to drive off any contaminating water. After cooling to 80° C., 11.2 grams of anhydrous chromium (III) chloride is added over a period of 20 minutes. The temperature of the mixture is raised slowly to 230° C. over a period of 6.5 hours before being cooled. The mixture is then stripped under a vacuum of about one millimeter of mercury at 160° C. to drive off unreacted acid and other volatiles. This gives a glassy green solid. The product is extracted from unreacted chromium (III) chloride and other insoluble material with three 100 cc. portions of diethyl ether, filtered, and stripped under vacuum.

Triisobutylaluminum is used as received from the manufacturer.

To an approximately ten percent by weight solution of triisobutylaluminum in heptane is added 1.0 mole equivalent of distilled water, stedily, but in one batch, while cooling the flask containing the solution with ice water to maintain a temperature of about 10° C. to about 20° C. The solution is stirred vigorously during and after water addition and continued until no further gas evolution is observed. This solution is added to the chromium (III) tris(2-ethylhexanoate) dissolved in about 50 milliliters of heptane, under argon, in a pre-dried 300 milliliter stainless steel autoclave, followed by the ligand additive to provide a certain mole ratio of ligand to chromium. The autoclave is thoroughly degassed with argon, then, ethylene, and pressurized with ethylene. The autoclave is heated to the desired temperature (see below) and additional ethylene is added to bring the autoclave to the desired final pressure in the range of 400 to 500 psig. As consumption of ethylene lowers the pressure, repressurization is repeated. The rate of ethylene consumption is typically 2000 grams per gram of chromium per hour at about 100° C.

After cooling, exceeds ethylene is vented, collected, and quantified. The ethylene consumed is determined by weighing before and after the reaction, with unreacted ethylene being determined by venting from the reactor into a liquid nitrogen trap. Volatile products are distilled from the polymer and catalyst residues and determined by gas chromatography using cyclohexane as an internal standard. The polymer cannot be quantified directly since it is contaminated with catalyst residues, but is obtained by difference, and this value is estimated by weighing the polymer and the catalyst residues and subtracting the catalyst residues from the total weight of involatile products. Selectivities are normalized to 100 percent. The components are introduced into the autoclave to provide 0.1 or 0.2 millimole of chromium; 5 to 1Q millimoles of aluminum plus water; and aluminum/chromium mole ratio of 50 to 1; and a ligand additive/chromium mole ratio as in Table I; and a triisobutyl aluminum/water mole ratio of 1. The trimerization is run in approximately 75 milliliters of heptane solvent at a temperature in the range of 70° C. to 140° C. The temperature is selected to give a suitable reaction rate.

The product obtained contains 1-hexene and polyethylene in a combined total of at least 98 percent by weight based on the weight of ethylene consumed. The balance of the product is represented by undefined octenes, 1-butene, and cis and trans 2-butene.

The above procedure is repeated for the ligand additives in the ranges set forth in Table I. The "range examined" refers to the ligand to chromium mole ratio. The procedure is repeated for the outer limits of the range and for several intermediate points. The point of best selectivity observed in the range is set forth in parenthesis in the same column. The selectivity given is for this point in the range. As noted, selectivity is the percentage by weight of 1-hexene recovered based on the weight of the ethylene consumed.

TABLE I

| ligand additive | range examined | selectivity |
| --- | --- | --- |
| monoglyme | 1 to 20 (10) | 64 |
| diglyme | 2 to 5 (2) | 59 |
| tert-butylisonitrile | 0.75 to 3 (2) | 52 |
| triglyme | 2 to 5 (2) | 50 |
| tetrahydrofuran | 5 to 15 (7.5) | 40 |

EXAMPLE II

Catalyst synthesis is performed at all times under inert (argon or nitrogen) atmospheres using conventional air-free techniques.

Chromium (III) tris(2-ethylhexanoate) is prepared as in Example I.

Chromium (II) bis(2-ethylhexanoate) is prpared by the addition of an equimolar mixture of triethylamine and 2-ethylhexanoic acid in heptane to a suspension of 0.5 mole anhydrous chromium (II) chloride in heptane. A slow reaction results in the formation of a deep purple solution and the precipitation of triethylammonium hydrochloride. The product is isolated as a purple oil after removal of the precipitate by filtration and the volatiles under vacuum.

A more general technique for the preparation fo chromium (II) carboxylates is as follows: to a stirred suspension of anhydrous chromium (II) chloride in dried, distilled, deoxygenated heptane or other similar solvent is added a mixture of 1.8 to 2.0 mole equivalents (based on chromium; 90 to 100% of that required for the correct stoichiometry) of each of the carboxylic acid and triethylamine, which had been stirred together in heptane for about 10 minutes. A slow reaction takes place resulting in the dissolution of most of the chromium chloride; the precipitation of a white solid believed to be triethylammonium hydrochloride; and the production of a deep purple or blue (in the case of trifluoroacetic acid, for example) solution. The mixture is then filtered to remove the precipitate, and the solvent and other volatiles are removed under vacuum. The product is extremely air sensitive in solution and is stored and manipulated at all times under an inert atmosphere of argon or nitrogen. Before use, a solution of known concentration in heptane is made, and aliquots are taken as required.

Chromium (IV) tetra-tertiary-butoxide is prepared as follows: 0.5 cc. (2.72 millimoles) of di-tert-butylperoxide is added to 10 cc. of distilled deoxygenated toluene. 0.19 gram (0.91 millimoles) of bis(benzene) chromium is then added, and the mixture is heated to about 90° C. for about 23 hours. The mixture is then stripped of volatiles under vacuum to give a green solid. The green solid is sublimed under reduced pressure to give the product as a low melting blue solid.

Example I is repeated. Table II sets forth the catalyst composition, temperature, selectivity to 1-hexene, amount of 1-hexene produced, time for each run, and hydrolysis ratio.

In Table II:
1. III is chromium (III) tris(2-ethylhexanoate).
2. IV is chromium (IV) tetra-tertiary-butoxide.
3. II is chromium (II) bis(2-ethylhexanoate).
4. Al is triisobutylaluminum.
5. Glyme is monoglyme.
6. The catalyst composition is given in millimoles.
7. Selectivity to free 1-hexene is calculated on (i) weight of ethylene consumed or (ii) weight of 1-hexene divided by weight of 1-hexene plus weight of polymer, the quotient being multiplied by 100 percent. The value is given in weight percent.
8. Time is the time of the run in minutes.
9. Temperature in degrees Centigrade and weight of 1-hexene produced, in grams, is self-explanatory.
10. Hydrolysis ratio is moles of water per mole of aluminum compound introduced during hydrolysis of triisobutyl aluminum.

TABLE II

| Catalyst Composition | | | Temperature (°C.) | Selectivity (wt. %) | 1-hexene (grams) | time (min.) | Hydrolysis ratio |
| --- | --- | --- | --- | --- | --- | --- | --- |
| Cr | Al | Glyme | | | | | |
| III | | | | | | | |
| 0.11 | 5.4 | 0.54 | 90 | 58 | 6.1 | 140 | 1.00 |
| 0.11 | 5.4 | 0.11 | 80 | 6 | 0.8 | 55 | 1.00 |
| 0.11 | 5.4 | 2.1 | 130 | 38 | 3.8 | 40 | 1.00 |
| 0.11 | 5.4 | 1.1 | 100 | 67 | 6.2 | 75 | 1.00 |
| 0.11 | 5.4 | 1.1 | 105 | 73 | 8.9 | 65 | 1.00 |
| 0.11 | 5.3 | 0.84 | 100 | 62 | 5.0 | 50 | 1.00 |
| 0.11 | 5.5 | 1.4 | 100 | 60 | 6.4 | 60 | 1.00 |
| 0.11 | 5.3 | 1.23 | 105 | 62 | 6.1 | 90 | 1.00 |
| 0.2 | 6.0 | 1.0 | 105 | 63 | 7.5 | 60 | 1.00 |
| 0.2 | 6.0 | 1.6 | 105 | 48 | 8.3 | 20 | 1.00 |
| 0.2 | 6.0 | 2.0 | 102 | 76 | 10.6 | 35 | 1.00 |
| 0.2 | 6.0 | 2.0 | 95 | 75 | 11.4 | 45 | 1.00 |
| 0.2 | 6.0 | 2.4 | 95 | 79 | 9.5 | 25 | 1.00 |
| 0.2 | 6.0 | 2.4 | 100 | 65 | 4.2 | 160 | 1.00 |
| 0.3 | 9.0 | 3.6 | 100 | 63 | 7.1 | 140 | 1.00 |
| 0.2 | 6.1 | 3.0 | 95 | 82 | 8.8 | 60 | 1.00 |
| 0.2 | 6.0 | 2.0 | 95 | 71 | 9.7 | 80 | 1.00 |
| 0.2 | 6.0 | 2.0 | 95 | 75 | 7.6 | 25 | 0.95 |
| 0.2 | 6.0 | 2.0 | 95 | 73 | 10.9 | 20 | 0.90 |
| 0.2 | 6.0 | 2.0 | 95 | 79 | 10.9 | 15 | 0.85 |
| 0.2 | 6.0 | 2.0 | 95 | 74 | 12.4 | 10 | 0.80 |
| 0.2 | 6.0 | 2.0 | 80 | 53 | 5.0 | 25 | 0.70 |
| 0.06 | 10.0 | 2.1 | 100 | 63 | 4.1 | 80 | 1.00 |
| 0.08 | 10.0 | 2.0 | 100 | 60 | 4.1 | 45 | 1.00 |
| 0.1* | 5.0 | 1.4 | 102 | 65 | 11.5 | 100 | 1.00 |
| 0.1* | 5.0 | 1.0 | 97 | 65 | 10.1 | 35 | 1.00 |
| IV | | | | | | | |
| 0.14 | 5.0 | 1.0 | 100 | 65 | 6.4 | 170 | 1.00 |
| 0.2 | 6.0 | 2.0 | 95 | 71 | 10.7 | 60 | 1.00 |

TABLE II-continued

| Catalyst Composition | | | Temperature (°C.) | Selectivity (wt. %) | 1-hexene (grams) | time (min.) | Hydrolysis ratio |
|---|---|---|---|---|---|---|---|
| Cr | Al | Glyme | | | | | |
| 0.2 | 4.0 | 2.0 | 102 | 80 | 14.8 | 175 | 1.00 |
| 0.2 | 6.0 | 2.4 | 100 | 62 | 10.8 | 90 | 1.00 |
| II | | | | | | | |
| 0.2 | 4.0 | 1.0 | 95 | 76 | 12.3 | 25 | 1.00 |
| 0. | 4.0 | 1.0 | 95 | 70 | 9.5 | 65 | 1.00 |
| 0.2 | 4.0 | 1.5 | 95 | 70 | 9.1 | 40 | 1.00 |
| 0.2 | 4.0 | 2.0 | 100 | 70 | 9.3 | 50 | 1.00 |
| 0.2 | 4.0 | 1.5 | 100 | 75 | 9.3 | 70 | 1.00 |
| 0.2 | 4.0 | 2.0 | 95 | 68 | 8.5 | 70 | 1.00 |
| 0.2 | 4.0 | 2.4 | 100 | 55 | 5.8 | 285 | 1.00 |
| III | | | | | | | |
| 0.43 | 21.4 | 4.3 | 125 | 46 | 6.0 | 120 | 1.00 |
| | | Triglyme | | | | | |
| 0.11 | 5.3 | 0.21 | 107 | 67 | 7.3 | 60 | 1.00 |
| 0.1 | 5.2 | 0.5 | 125 | 40 | 3.3 | 35 | 1.00 |
| | | Diglyme | | | | | |
| 0.11 | 5.3 | 0.21 | 105 | 57 | 5.8 | 30 | 1.00 |
| 0.11 | 5.3 | 0.53 | 140 | 55 | 3.6 | 140 | 1.00 |
| | | THF | | | | | |
| 0.1 | 5.2 | 5.2 | 100 | 35 | 4.4 | 80 | 1.00 |
| 0.11 | 5.3 | 0.8 | 115 | 49 | 1.5 | 60 | 1.00 |
| 0.1 | 5.4 | 1.1 | 110 | 60 | 6.3 | 105 | 1.00 |
| 0.11 | 5.4 | 1.6 | 120 | 46 | 1.8 | 255 | 1.00 |
| | | TBIN | | | | | |
| 0.2 | 10.1 | 0.15 | 70 | 35 | 4.5 | 25 | 1.00 |
| 0.2 | 10.3 | 0.3 | 70 | 52 | 5.3 | 60 | 1.00 |
| | | Veratrole | | | | | |
| 0.11 | 10.8 | 0.55 | 90 | 23 | 2.0 | 70 | 1.00 |
| 0.11 | 5.4 | 1.1 | 100 | 41 | 1.8 | 15 | 1.00 |
| | | TMEDA | | | | | |
| 0.11 | 5.5 | 0.22 | 140 | 32 | 1.0 | 190 | 1.00 |
| 0.11 | 5.4 | 0.11 | 120 | 27 | 1.7 | 130 | 1.00 |
| | | DEE | | | | | |
| 0.1 | 5.2 | 1.0 | 100 | 5 | 0.6 | 50 | 1.00 |
| 0.1 | 5.3 | 2.1 | 80 | 10 | 1.3 | 60 | 1.00 |
| 0.1 | 5.3 | 5.3 | 90 | 15 | 2.0 | 84 | 1.00 |
| 0.11 | 5.3 | 21.2 | 100 | 22 | 3.2 | 70 | 1.00 |

*Run conducted in 1-hexene solvent instead of heptane.
THF = tetrahydrofuran
TBIN = tert-butylisonitrile
Veratrole = ortho-dimethoxybenzene
TMEDA = tetramethylethylene diamine
DEE = diethyl ether

I claim:

1. A catalyst comprising the reaction product of (i) a chromium compound, which will provide active catalytic species under trimerization conditions; (ii) a hydrocarbyl aluminum hydrolyzed with about 0.8 to about 1.1 moles of water per mole of aluminum compound; and (iii) a donor ligand selected from the group consisting of hydrocarbyl isonitriles, amines, and ethers wherein the catalyst has an aluminum to chromium mole ratio in the range of up to about 200 to one and a ligand to chromium mole ratio in the range of up to about 100 to one.

2. The catalyst defined in claim 1 wherein (i) the oxidation state of the chromium in the chromium compound is selected from the group consisting of (II), (III) and (IV); (ii) the hydrocarbyl aluminum is represented by the formula $R_3Al$ wherein each R is an alkyl, cycloalkyl, or hydride radical; at least one R is a hydrocarbyl radical; two or three R radicals can be joined in a cyclic radical; each R can be alike or different; and each R, which is a hydrocarbyl radical, has 1 to 20 carbon atoms; and (iii) the hydrocarbyl portion of the ligand has 1 to 20 carbon atoms and can be straight or branched chain alkyl, cycloalkyl, or aromatic, or a mixture thereof.

3. The catalyst defined in claim 2 wherein the non-metallic portion of the chromium compound is an alkoxy, ester, or ketone radical; the hydrocarbyl aluminum is an aluminum trialkyl or triaryl; and the ligand is selected from the group consisting of $CH_3O(CH_2CH_2O)_nCH_3$ wherein n is 1, 2, or 3; tert-butyl isonitrile; tetrahydrofuran; and $C_6H_4(OCH_3)_2$.

4. The catalyst defined in claim 1 wherein the donor ligand is incorporated into the hydrocarbyl aluminum structure.

5. A process for preparing a catalyst comprising reacting (i) a chromium compound, which will provide active catalytic species under trimerization conditions, (ii) a hydrocarbyl aluminum hydrolyzed with about 0.8 to about 1.1 moles of water per mole of aluminum compound, and (iii) a donor ligand selected from the group consisting of hydrocarbyl isonitriles, amines, and ethers in amounts sufficient to provide an aluminum to chromium mole ratio in the range of up to about 200 to one and a ligand to chromium mole ratio in the range of up to about 100 to one.

6. The process defined in claim 5 wherein the chromium compound is a chromium (II) carboxylate.

7. The process defined in claim 6 wherein the chromium (II) carboxylate is prepared by the reaction of chromium (II) chloride, a carboxylic acid, and triethylamine in an inert organic solvent.

8. The process defined in claim 5 wherein the donor ligand is incorporated into the hydrocarbyl aluminum structure.

9. The catalyst defined in claim 1 wherein the aluminum to chromium mole ratio is in the range of about one to one to about 100 to one.

10. The catalyst defined in claim 1 wherein the ligand to chromium mole ratio is in the range of about one to one to about 100 to one.

11. The catalyst defined in claim 1 wherein the ligand to chromium mole ratio is in the range of about one to one to about 40 to one.

* * * * *